United States Patent [19]
Peterson

[11] Patent Number: 5,279,167
[45] Date of Patent: Jan. 18, 1994

[54] METHOD AND APPARATUS FOR PROVIDING A SAMPLE FOR TESTING FOR VOLATILE EMISSIONS

[76] Inventor: Roger Peterson, Rte. 1 Box 315, Sweeny, Tex. 77480

[21] Appl. No.: 895,788

[22] Filed: Jun. 9, 1992

[51] Int. Cl.⁵ .............................................. G01N 1/14
[52] U.S. Cl. .................. 73/863.86; 73/864.34; 73/864.74
[58] Field of Search ........... 73/863.84, 864.34, 863.86, 73/864.74

[56] References Cited

U.S. PATENT DOCUMENTS

| | | | |
|---|---|---|---|
| 2,844,964 | 7/1958 | Guibert | 73/863.86 |
| 3,566,865 | 3/1971 | Hay | 73/863.83 |
| 3,896,673 | 7/1975 | Audouze et al. | 73/864.34 |
| 4,307,620 | 12/1981 | Jiskoot | 73/863.83 |
| 4,413,533 | 11/1983 | Diesel | 73/863.86 |
| 4,674,343 | 6/1987 | Larson | 73/863.86 |
| 4,791,821 | 12/1988 | Spencer | 73/864.74 |
| 4,823,623 | 4/1989 | Carpenter et al. | 73/864.74 |
| 4,879,915 | 11/1989 | Spencer | 73/864.74 |
| 4,939,940 | 7/1990 | Tsukida | 73/864.74 |
| 4,986,138 | 1/1991 | Spencer | 73/863.86 |
| 5,003,830 | 4/1991 | Spencer | 73/863.83 |
| 5,029,485 | 7/1991 | Marr | 73/864.34 |
| 5,038,623 | 8/1991 | Zeh | 73/863.83 |
| 5,060,529 | 10/1991 | Bals et al. | 73/864.74 |
| 5,092,988 | 3/1992 | Womack et al. | 73/864.34 |

FOREIGN PATENT DOCUMENTS

| | | | |
|---|---|---|---|
| 0725235 | 9/1942 | Fed. Rep. of Germany | 73/863.83 |
| 2918768 | 11/1980 | Fed. Rep. of Germany | 73/863.83 |
| 2343239 | 9/1977 | France | 73/863.83 |
| 0868429 | 9/1981 | U.S.S.R. | 73/863.83 |

OTHER PUBLICATIONS

Dopak, Inc. advertisements pp. 1-34.

*Primary Examiner*—Hezron E. Williams
*Assistant Examiner*—George M. Dombroske
*Attorney, Agent, or Firm*—Gunn & Kuffner

[57] ABSTRACT

The present disclosure is directed to a sample collecting and storing apparatus. A metal cabinet encloses a hand operated, chain driven pump connected serially with inlet and outlet lines providing a closed loop flow with a large tank to be sampled. The pump connects serially with a three port, two position valve mechanism defining a bypass. Another port of the valve serially connects with an industry standard fitting which in turn connects with the head of a syringe positioning a needle tip in alignment with the valve. A suitable mounting bracket supports the valve and associated syringe in conjunction with a second syringe preferably bent in a 90° angle and having fittings for the syringe. This defines a second syringe tip so that two syringe needles insert through a septum into a sample receiving container. A method of operation is also set forth.

11 Claims, 3 Drawing Sheets

METHOD AND APPARATUS FOR PROVIDING A SAMPLE FOR TESTING FOR VOLATILE EMISSIONS

The present disclosure is directed to a sample taking technique and also an apparatus which enables taking of a sample. It is particularly useful as a portable device which can be moved to and from remote sites where samples are required even where samples are required without any available electricity. Indeed, electrical power is avoided. It is a device which can be used to sample a fixed tank or container which must be tested or assayed to vouch for the purity of the material in the sample container. It can be used with both liquid and gas samples. Likewise, it can be used with a fixed tank or a moveable tank such as a rail tank car, or perhaps a tank in a barge.

The present apparatus is particularly useful in obtaining a sample for testing purposes without opening the lid or hatch on a container. There is a risk that dangerous fumes can be released upon cracking the lid or cover of a liquid or gas storage vessel. For instance, a liquid may create volatile fumes which are either poisonous or explosive.

They may create problems for nearby personnel, vegetation, cattle, livestock or wild life, or any other of a number of problems. In addition, some volatile discharges do not create a problem for anyone near the products but rather disperse in the atmosphere and create problems in the atmosphere, for instance, in airborne pollution, ozone depletion and the like. Suffice it to say, these problems are epidemic and create such difficulties that safety and personnel protection are paramount. Accordingly, the present disclosure sets forth an improved system for taking samples to avoid accidental release of vapors.

The present disclosure shows a structure cooperative with and coordinated with a storage tank or vessel having an internally located system which, more specifically, is permanently installed, is provided with quick disconnect fittings, and incorporates multiple lines extending to different depths of a storage or transportation vessel. More specifically, this set of equipment is utilized so that, as often as needed, the present apparatus can be connected to draw a sample or specimen from the interior. The sample or specimen is placed in a small container for easy testing at a remote location such as a laboratory. To get to the laboratory, a sample vessel must be taken to the site of the tank, filled with the sample and then removed to the testing laboratory. This provides small, easily handled samples.

The present system contemplates the use of a sample container having a protective lid which, when removed, exposes a septum over the mouth of a shatter proof container so that the material making up the sample is captured on the interior. This material is delivered by means of syringe needles which are inserted through the septum. Moreover, the syringe needles provide two paths through the septum, one to introduce the sample and the second to remove the gas originally in the sample container. The two needles cooperate with a valve mechanism supported on an upstanding frame. One needle is connected directly with the valve and serves as an inlet. The valve is a two position, three way valve providing an alternate port for recirculation. Moreover, the valve is constructed and positioned by means of a mounting mechanism so that the valve provides flow directly out of the valve into an industry approved fitting connecting directly to a straight needle for injection of the sample. By contrast, a bent needle is provided which enables gas circulation from the sample container flowing in the bent needle connected through another industry standard fitting and out through a flow line assembled of industry standard fittings. The valve and the associated fittings are constructed on a mounting mechanism which aligns the needles so that the needles are in close proximity to form the necessary perforations in the septum for injection into the container. Moreover, this type arrangement is able to deliver the vented or voided gas flow for circulation back towards the storage vessel. For instance, the storage vessel which is being sampled may hold a very large volume. When the present apparatus is connected with it, the volume of sample flow delivered is relatively small. Accordingly, a highly reliable delivery system for transfer of gas sample to and from the large storage vessel is readily provided in this apparatus. Moreover, this apparatus provides a mechanism which can readily pump the required sample. Pumping is accomplished by means of a portable structure which is suitably hand carried to a field location so that the sample can be readily extracted in all kinds of field locations, in all kinds of inclement weather, and with all kinds of risks relatively safe handled. For instance, if the sample is a gas which is explosive when exposed to atmosphere, the present apparatus accommodates that problem by the incorporation of a sample collection mechanism which features the twin needle system just mentioned as well as a pump which is hand operated substantially without risk of electrical spark. It is preferably constructed without steel so that the whole of the structure is not able to form a spark. In addition to that, there is safety in the definition of the flow path. Escape of the sample gas to atmosphere is prevented. There is a closed flow path which extends through the equipment of this system serially connecting with a pump, then a valve, then the twin needle construction adjacent to the valve for delivery into the sample container and back to the storage tank. This route (provided substantially without chance of escape to the atmosphere) yields a system which is able to operate safely without creating fugitive gases which might otherwise escape to the atmosphere.

The present apparatus is summarized as a portable sample collection system which has an integrated pump, valve and twin needle delivery system. In a large housing which is sized to be hand carried, a hand crank provides power for a pump. The pump forces the sample gas through the equipment by delivery of the flowing sample from the pump into a two position, three port valve. In one position, the sample is delivered through a twin needle construction into a closed sample bottle. Moreover, the sample bottle is filled while the previously existent gas in the bottle is forced out through the twin needle construction. That defines a return flow path back to the storage tank. In the preferred embodiment, the twin needle construction is achieved by mounting twin needles on a bracket or frame work which supports the two position valve along with a valve actuator. The valve and frame work align the needles so that they may be jointly forced into the sample container. Moreover, the twin needle construction utilizes approved standard fittings which are leak proof and which are also known to provide quality sealing for the sample collection system. The apparatus is portable, being provided with a pair of hoses which terminate at disconnect fittings for communication with the storage tank.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
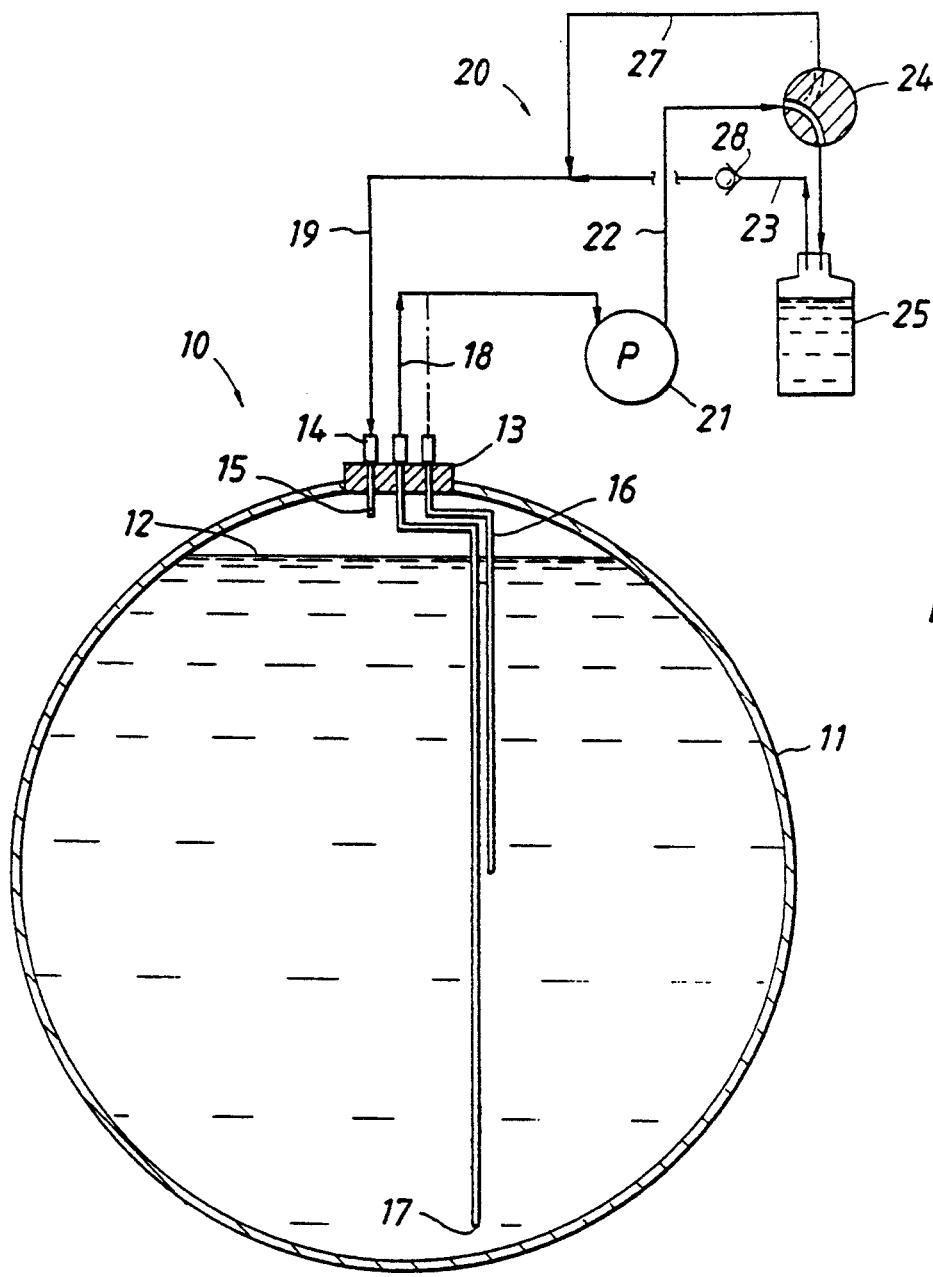
FIG. 1 is a schematic fluid flow system showing a mode of connection of a storage tank or the like with the sample taking apparatus of the present disclosure wherein the sample tank is sampled to place a measured portion in a small sample container through use of the present apparatus.

Attention is first directed to FIG. 1 of the drawings where the numeral 10 identifies a sample collection system in schematic form. This will be described first and then the apparatus of the present disclosure will be specifically detailed. More specifically, a description of FIG. 1 sets forth the nature of the problem to be solved and the manner in which the present apparatus is connected for sample collection. Accordingly, the system shown in FIG. 1 incorporates a storage tank 11. This tank can be fixed or mobile, the later being exemplified by a barge or tank car. A liquid 12 is shown in the tank 11 and is filled in the tank to some depth. Alternately, the tank can be filled with a gas such as chlorine gas or the like. The cargo in the tank 11 can cover a wide range of materials including those which are explosive, those which might be poisonous, and those which have other undesirable effects. A wide range of examples can be readily listed. The tank 11 incorporates a hatch 13 which is permanently installed and connects with disconnect fittings 14. One line 15 connects to the head space in the tank. The line 15 is very short. By contrast, the line 16 is quite long so that one can obtain a sample from the middle portions of the tank. The longest line 17 extends to the bottom of the tank so that materials at the bottom can be collected. This is important to especially obtain different samples should there be a stratification of materials in the tank. For instance, if the tank is filled with oil and water, the oil will float to the top, the water will settle to the bottom, and the two will define a phase separation depending on the relative volume of the two mixed in the tank 11. It is therefore important to be able to get a sample from the bottom to identify the nature and amount of impurities which may collect at the bottom of the tank. Sometimes, the material removed from the deep sample line 17 is very important.

External to the storage tank which may hold thousands of gallons of gas or liquid, the present apparatus is connected by access to the disconnect fittings 14. A sample line 18 is connected to deliver sample from one of the disconnect fittings. This will vary depending on the stage of filling and the time of taking the sample. Suffice it to say, the illustrated connection is not necessarily the only mode of connection. In any event, the sample line 18 is connected for delivery of sample to the system, there being also a return line 19 which returns surplus sample back to the storage tank 11. In addition, and as will be described on purging of these small lines, any gas which may be in these small lines 18 and 19 is also returned to the head space above the liquid 12 in the tank 11. Relative scale of the tank 11 compared to the size of the sample to be obtained is quite large; the tank 11 can easily comprise the entire cargo of a large barge while the present system involves purging of lines which hold less than one liter of gases. In any case, the lines 18 and 19 connect with the disconnect fittings 14.

The numeral 20 generally identifies the sample collection apparatus of this disclosure. It includes all of the equipment above the hatch 13 including the sample line 18 and the return 19 which are typically supplied with suitable length to reach the fittings 14. These lines can be a few feet in length typically. This apparatus 20 is shown in schematic form in FIG. 1. To this end, the sample collection apparatus 20 incorporates a pump 21 which draws sample through the line 18 and forces it under positive pressure through the line 22. Moreover, fluid flow through the line 22 is provided to a valve 24 which is defined in greater detail hereinafter as a two position, three port valve. This delivers fluid flow into a sample container 25. Several such containers can typically be filled from one or several samples taken from a particular tank 11. The container 25 is small, typically on the size of one half liter, perhaps one liter in volume. The valve 24 is operated so that sample is delivered into the storage container 25. As it is forced into the container 25 under operation of the pump 21, any gas in the container 25 is forced out through a line 23 which connects with the return line 19 through a check valve 28. In addition to that, the three way valve connects with another line 27 which is a bypass line, avoiding filling of the container 25 so that the valve 24 can connect the pump 21 through the bypass line 27 back into the return line 19. When the pump 21 is operated, all fluid which is pumped by it ultimately is directed to the return line 19 except that portion which is captured and kept in the sample container 25. Gas in the lines 18, 19, 22, 23 and 27 is also returned to the head space in the tank 11. The valve 24 is operated so that a sample is delivered into the storage container 25 during operation of the pump 21. Any gas originally present in the container 25 is forced out through the return line 19. To avoid filling of the container 25, for example, the valve 24 can be set to a "circulating" position to conduct fluid from the pump 21 through the valve 24 into the by pass line 27 which is connected to the return line 19 back to the tank. To prevent back flow from the by pass line into the sample container through line 19, a check valve 28 is provided in the return line 19 upstream of the by pass line 27. The check valve allows fluid to flow from the sample container 25 into the storage tank through the line 19, but will prevent return flow of fluid from line 27, or the downstream side of line 19, back into the sample container 25.

Figure 2:
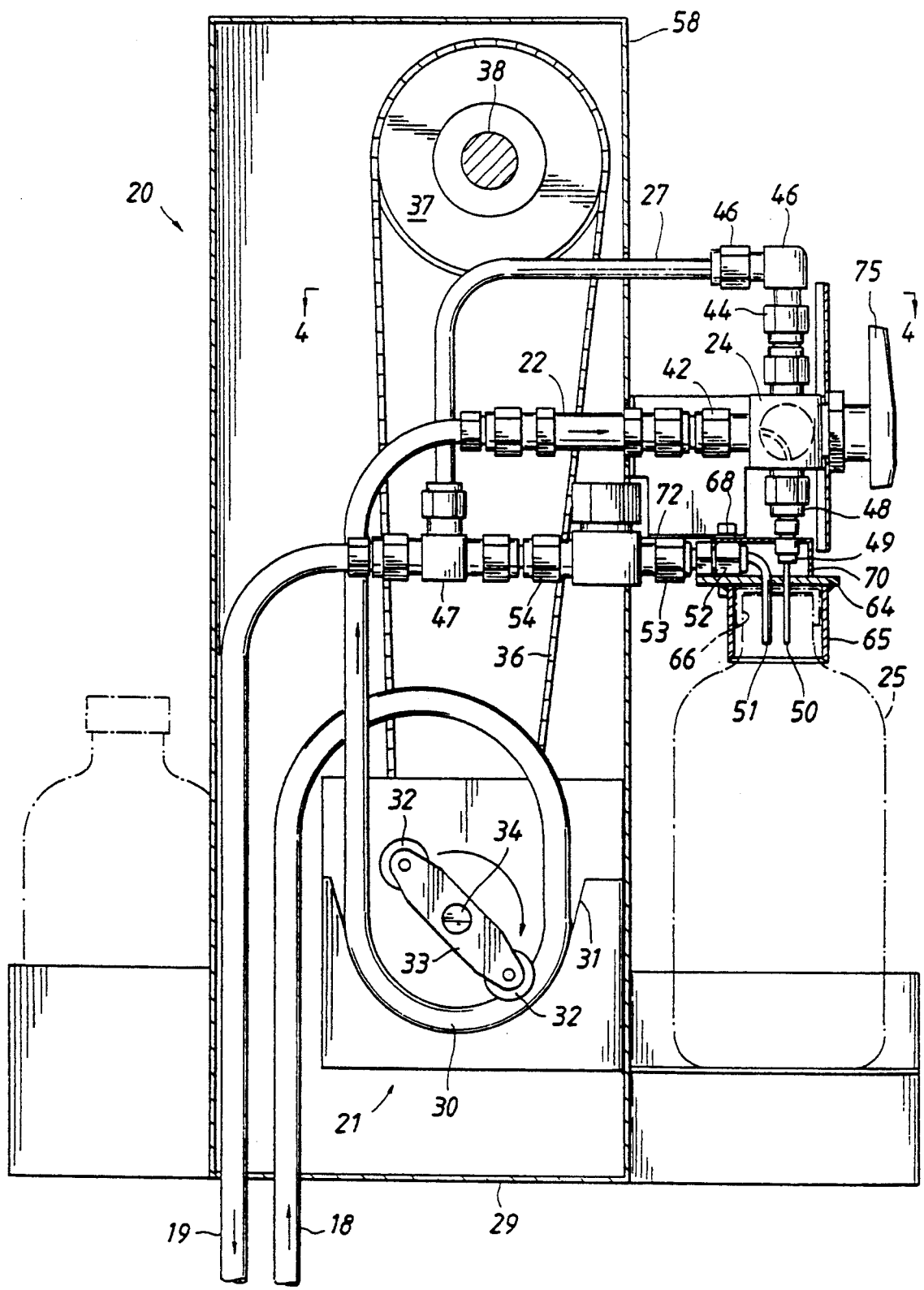
FIG. 2 of the drawings is a side view, a portion of the cabinet broken away for sake of clarity, of the present apparatus illustrating the deployment of the pump, valve, connections, and a twin needle support mechanism to place a vaporous sample in a sample container.

Attention is now directed to FIG. 2 of the drawings which will be described in detail. The description will proceed beginning with the sample line 18 which is input to the device. The sample line 18 is connected with the fitting previously mentioned and extends into this structure. The structure has the form of a cabinet or housing 29 which is sheet metal, preferably formed of stainless steel, and formed into a cabinet or enclosure. Conveniently, the sample line 18 can enter at any location but is shown entering through the bottom, extends upwardly and is looped into a bight 30. The bight 30 is captured on a curving track 31 which has the form of a semicircle. The bight of tubing is captured against the semicircular wall so that a roller 32 supported on an arm 33 can rotate about a mounting shaft 34. The roller 32 is duplicated at the opposite end of the arm 33. When the rollers are moved in the direction of the arrow shown in FIG. 2, they roll or pinch the bight of the tubing, thereby creating a pumping action. It is noteworthy that the fluid in the sample line never leaves the sample line. Accordingly, this type of pump is desired to hold down leaks or unintended emissions from the pump. This type of pump, sometimes known as a peristaltic pump, is mounted fixedly to the cabinet 29 and is provided with a sprocket (not shown) on the far side of the pump 21 so that it can be hand powered by a drive chain 36. The chain 36 extends upwardly to a drive sprocket 37 (see FIG. 3) in the upper part of the cabinet, the sprocket 37 being mounted on a shaft 38. The shaft extends through the cabinet, and is connected with a hand crank 40 on the exterior of the cabinet 29. Moreover, the sprocket 37 is supported or journaled onto the shaft 38 shown in FIG. 3. The shaft is supported at both ends of the shaft for easy rotation. This provides the appropriate alignment where the operator can turn the crank 40 and thereby provide a pumping action at a time when the operator wishes it to occur. As further shown in FIG. 3 of the drawings, the hand crank is exposed on the exterior so that a few turns by the operator can provide an adequately sized sample. Going back to FIG. 2 of the drawings, it will be further observed that the pump 21 provides the pressurized flow through the line 22 which is then input through appropriate fittings 42 into the body of the valve 24. The valve 24 has an internal valve element represented in dotted line in FIG. 2 of the drawings which is provided with three ports. The inlet port is connected to the fitting 42 for delivery of the sample of interest. The valve 24 includes a bypass outlet which connects through the fitting 44 on the top of the valve body as shown in FIG. 2. That connects with an elbow 45 and then another fitting 46. In turn, that connects with the bypass line 27 previously mentioned and that is then supplied to a tee 47. The tee is connected to the return line 19.

Going back to the valve construction, the bypass port is on the top side while there is a duplicate port on the bottom side. That port connects with an industry standard fitting 48. In turn, that supports a mounting nut 49 and an injection syringe 50 extends from that. The mounting nut 49 holds or captures the syringe 50. The syringe is a purchased item equipped with a base enabling capture and mounting, thereby positioning the syringe tip where the sample is introduced into the storage container 25. Details of construction will be given later.

As described to this juncture, the sample gas or liquid is delivered through the valve into the storage container 25. In addition to that the return path should be considered. The return path removes gas that was originally in the container 25. In addition, any filling is removed along this path also. This incorporates the syringe needle 51. It is bent into a 90° bend for removal of the vented gas or liquid. As shown in FIG. 2, the relative diameters of the syringe needles 50 and 51 are somewhat enlarged for purposes of illustration. Moreover, the return syringe needle is provided with the same type of industry standard mounting head and connects with a common or industry standard fitting 52. The fitting 52 is at right angles with respect to the valve 24 and the fitting 48 on the bottom side of that valve. This is done so that there is clearance for the relatively small needles over the mouth of the bottle which again is a relatively small bottle. To avoid crowding, the return syringe needle is bent thereby permitting greater access for the fittings involved in the return needle construction. More specifically, the fitting 52 is aligned with another fitting 53 providing a serial connection, and that in turn connects with the tee 47 by means of the connectors 54. Physically, the tee is aligned so that it connects with the fitting 52. This accommodates a fixed or rigid structure from the fitting 52 and including the tee 47. In turn, that is accommodated by a flexible bypass line 27 as illustrated in FIG. 2 of the drawings.

CONSTRUCTION OF THE VALVE MOUNTING MECHANISM

Figure 4:
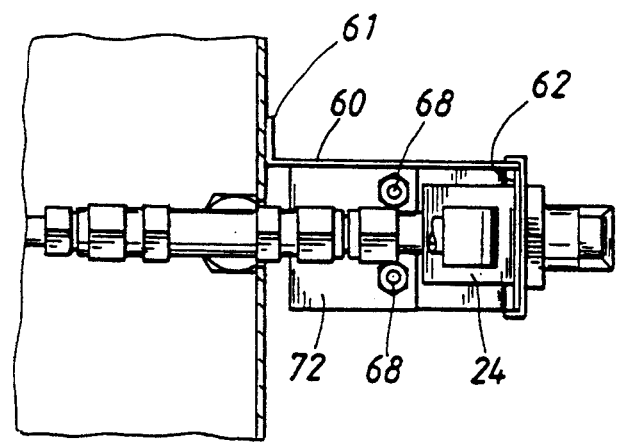
FIG. 4 is a sectional view taken along the line 4—4 of FIG. 2 of the drawings showing details of construction of the twin needle support bracket and the cooperative two position valve.

The numeral 58 identifies the front face of the cabinet 29. The valve 24 is positioned forwardly of this front face and is mounted on a protruding bracket 60 which is better shown in FIG. 4 of the drawings. The bracket 60 includes a flange 61 which can be conveniently tack welded or otherwise joined to the front panel 58. Moreover, it extends forwardly, and supports a mounting tab 62 which supports the valve body 24. The body is fixed to this as shown in FIGS. 2 and 4 considered jointly. For purposes of careful alignment, this locates the valve body at a spaced distance forwardly of the cabinet so that the bottle 25 can be positioned below it as illustrated in FIG. 2. In addition to that, this locates the valve body so that there is a straight connection downwardly through the fitting 48. The fitting 48 ultimately supports the syringe needle 50. That needle is positioned through a hole in a plate 64 shown in FIG. 2, and the plate 64 in turn supports a ring 65. The ring 65 is sized to fit around the neck of the bottle 25. The bottle 25 is normally provided with a metal cap or cover (not shown) which provides physical protection for a septum 66 which is exaggerated in thickness in FIG. 2 of the drawings to illustrate its location. The needle 50 punctures the septum. This puncture is self healing when the narrow gauge needle is removed from the septum. The needle 50 therefore is free of the plate 64 but passes through a hole in that plate with modest clearance. This plate serves as an alignment mechanism to direct the syringe needle properly into the septum. In turn, the plate 64 is incorporated below the mounting bracket 60 and is joined to it by suitable fasteners including the upstanding bolts 68 shown in FIG. 4 of the drawings. These align the plate 64 and hold it stationary in conjunction with the spacer bracket 70 shown in FIG. 2 of the drawings. The bracket 70 extends in the fashion of a U shaped plate over the plate 60 there being space between the two for the fitting 52. This helps lock the fitting 52 relative to the plate 60, so that it also is fixed in location and cannot move or slide. In turn, that anchors the support structure for the bent syringe needle 51. That in turn provides the necessary anchoring and alignment so that the two syringe needles are parallel to each other.

Returning to FIG. 2 of the drawings, the bolts 68 extend upwardly so that a laterally projecting tab 72 at the lower marginal edge of the bracket 60 is also included. This member 72, better shown in FIG. 4 of the drawings, assures alignment of the L-shaped syringe needle.

Figure 3:
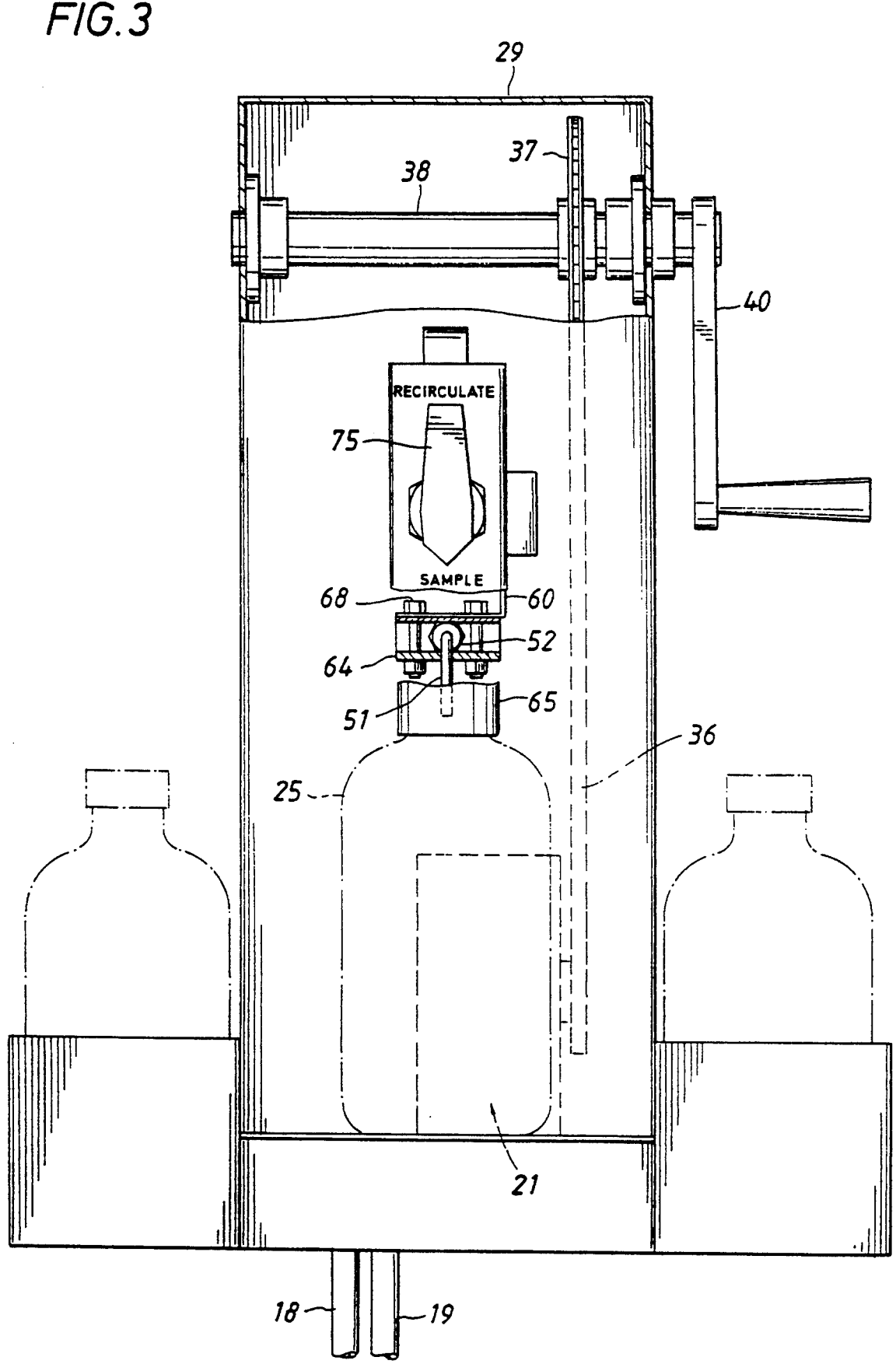
FIG. 3 is a front view of the apparatus shown in FIG. 2 of the drawings and further illustrating positioning of the twin needle construction immediately in front of the structure so that a sample container can be filled.

Going now to FIG. 3 of the drawings, this view perhaps adds a measure of clarity to the construction just mentioned which shows how the return syringe 51 is fixed and anchored in place. More importantly, it also shows the construction by which the syringe needle 51 is aligned with the circular collar 65 which positions over the neck of the bottle. Last of all, it also shows how the mounting bracket 60 supports and holds all of this equipment in proper alignment above the sample container 25. For the benefit of the operator, the face is imprinted with the appropriate operative legends, and a handle 75 is provided for the valve. The handle is mounted so that it is easily grasped by the user.

AN EXAMPLE OF OPERATION

Assume that the portable apparatus 20 of this disclosure is used to obtain a sample of an unknown liquid in the tank. The equipment is shown in FIG. 3 of the drawings in the fashion suggesting that several sample bottles can be carried with the cabinet. In any event, the portable equipment 20 is moved to the necessary location and the sample line 18 is made fast through the appropriate connector 14. Likewise, the return line 19 is connected. Once these connections are made, the next step is to remove the cap or lid from the sample container 25 and slide the sample container 25 upwardly so that the neck of the bottle is engaged by the circular collar 65 for alignment purposes. This automatically punctures the septum with both needles, and both needles are inserted into the container 25. By hand, the user then operates the pump 21 previously mentioned, cranking the pump for several turns. Before pumping is started, the valve is switched to the circulate position. This is the flow path illustrated in FIG. 1 of the drawings. Fluid flows in this path so that the line 18 is purged. The gas resident in the various lines and container 25 before starting is forced out of the lines and is removed by delivery through the return line 19. After operating the equipment for a few strokes on the pump, perhaps 10 revolutions or so, the operator can then switch the valve from the circulate position to the sample position, the sample is then introduced into the container 25. Indeed, this ability to control the valve and provide bypass fluid flow enables the operator to assure that an appropriate sample is obtained. Continued pumping after the sample has been obtained is also desirable to restore the fluid in lines back to the container 11. That is to say, the recirculation position is used to assure that the lines are properly purged, the right volume of sample is delivered to the container, and the sample is placed in the container 25. The pump can be rotated in the opposite direction to clear the liner by return flow.

After the sample has been removed and placed into the container 25, the container can be quickly disconnected simply by pulling it downwardly, relatively pulling away from the two syringe needle tips, and then the container 25 is recapped for safety sake. Another sample container can be filled again in the same fashion or for different reasons.

After completing the sample collection routine, the lines 18 and 19 can then be disconnected and stored so that the equipment 20 can be carried to another location. It is relatively light weight, especially in light of the construction of the valve mounting mechanism detailed in FIGS. 2 and 4. It is also relatively inexpensive in light of this type of fabrication.

While the foregoing is directed to the preferred embodiment, the scope is determined by the claims which follow:

I claim:

1. A portable system for use in obtaining a sample from a closed tank containing a gas or liquid therein wherein the portable system cooperates with the tank and comprises:
    (a) inlet and outlet lines connected through a pumping means for removing a sample from the tank flowing through the pumping means and circulating through the lines resulting from said pumping means operation;
    (b) valve connected with said inlet and outlet lines and pumping means wherein said valve has an inlet port and two outlet ports, one of the outlet ports defining an input for a bypass line;
    (c) a pair of elongate, extending syringe needles having tips located in near proximity to enable the tips to puncture and enter through a septum over a sample receiving container;
    (d) means for connecting said valve with one of said needles to support said needle and define a fluid flow path from said valve through said one of said needles for communication with the sample receiving container and further including support means fixedly holding said needle tips in fixed spatial relationship within said container, said support means enabling said needles to be supported externally of said container prior to insertion through the septum of the container; and
    (e) said support means comprises a bracket mounting said valve aligned over one of said needles to enable said container to be filled through said valve wherein said bracket comprises a pair of spaced plates capturing therebetween a fitting for the second of said needles.

2. The system of claim 1 wherein said pair of plates comprises bolt supported and spaced apart parallel plates supporting said valve, and said first needle extends through said plates.

3. The system of claim 1 wherein said bracket supports a downwardly directed, circular, container alignment means for temporary engagement with said container.

4. The system of claim 1 further including an upstanding front panel supporting a control for said valve.

5. The system of claim 4 including a valve body mounted on said front panel and having a bottom located outlet port and a fitting connected to said outlet port and then to said first needle.

6. The system of claim 5 wherein said first needle is connected by an "industry standard" fitting so that flow is directed downwardly through said needle and valve.

7. The system of claim 6 wherein said first needle is mounted solely on said fitting and extends through a pair of plates below said valve body.

8. The system of claim 7 wherein said pair of plates align said container to said first needle.

9. A method of removing a sample using inlet and outlet lines and a pumping means to obtain a sample from a tank holding a liquid or gas to be sampled from the tank, wherein the method comprises the steps of:
   (a) connecting inlet and outlet lines from a tank through a pumping means to enable sample circulation through said pumping means using said inlet and outlet lines;
   (b) providing sample flow from said pump means through a valve for a sample receiving container;
   (c) delivering sample through said valve into said sample receiving container by insertion of an elongate, straight syringe needle having a pointed tip enabling communication into the sample receiving container;
   (d) anchoring a second syringe needle in a fixed, angular relationship to said first syringe needle and then bending the second syringe needle having a pointed tip in near proximity to said first syringe needle to enable two syringe needle tips to be inserted into the sample receiving container; and
   (e) positioning the needles including pointed tips so that the needles are connected serially with the sample receiving container to admit sample into the container and to remove the atmosphere previously in the container by purging flow through said container so that the first and second needles are adjacent and yet spaced and are supported for aligned movement of the sample receiving container in one motion.

10. The method of claim 9 wherein the second syringe needle is anchored and aligned using an industry standard fitting for support.

11. The method of claim 10 wherein the step of anchoring includes clamping between a pair of clamping faces.

* * * * *